United States Patent [19]

Williams

[11] Patent Number: 5,612,226

[45] Date of Patent: *Mar. 18, 1997

[54] GAS/LIQUID CONTACT APPARATUS

[75] Inventor: Michael R. Williams, Burlington, Canada

[73] Assignee: LifeTech Corporation, Canada

[*] Notice: The term of this patent shall not extend beyond the expiration date of Pat. No. 5,366,696.

[21] Appl. No.: 538,199

[22] Filed: Oct. 3, 1995

Related U.S. Application Data

[63] Continuation of Ser. No. 173,001, Dec. 27, 1993, abandoned, which is a continuation-in-part of Ser. No. 1,630, Jan. 7, 1993, Pat. No. 5,366,696.

[51] Int. Cl.$^6$ ............................................. A61M 11/00
[52] U.S. Cl. .......................... 436/167; 422/45; 422/47; 435/2; 128/DIG. 3; 239/346
[58] Field of Search .................... 422/44–47; 435/2; 128/DIG. 3, 200.14, 200.18, 200.19, 200.21, 200.23; 239/346, 338, 432; 436/167

[56] References Cited

U.S. PATENT DOCUMENTS

| | | | |
|---|---|---|---|
| 2,827,901 | 3/1958 | Jones | 422/45 |
| 3,097,645 | 7/1963 | Lester | 239/338 |
| 3,104,062 | 9/1963 | Mahon | 239/346 |
| 3,584,792 | 6/1971 | Johnson | 239/338 |
| 5,062,419 | 1/1991 | Rider | 128/200.21 |

FOREIGN PATENT DOCUMENTS

4007867  9/1991  Germany.

*Primary Examiner*—Lyle A. Alexander
*Attorney, Agent, or Firm*—Klauber & Jackson

[57] ABSTRACT

A gas/liquid contact method and apparatus, for example, for oxygenating blood using $O_2$ and $O_3$. A low pressure stream of oxygen is introduced into a chamber through a spray orifice while inducing blood into the oxygen stream in a first blood/oxygen contact zone. The blood is caused to issue from the spray orifice as a dispersed low-pressure spray of blood droplets and is directed against a dome-shaped film forming surface located within the chamber in the path of spray. The droplets impinge on the surface at relatively low velocity and form a film for providing a further oxygen/blood contact zone. The apparatus may be designed to operate on a one-pass or a recirculation basis.

24 Claims, 4 Drawing Sheets

GAS/LIQUID CONTACT APPARATUS

CROSS-REFERENCE TO RELATED APPLICATIONS

This Application is a continuation of application Ser. No. 08/173,001, filed Dec. 27, 1993 now abandoned which is a continuation-in-part of application Ser. No. 08/001,630 filed Jan. 7, 1993, now U.S. Pat. No. 5,366,696.

FIELD OF THE INVENTION

The invention relates to a gas/liquid contact apparatus, for example, for oxygenating human blood. It is to be understood that the invention may also be used for contacting other gases and liquids.

BACKGROUND OF THE INVENTION

Oxygen is an allottopic element, the most common of which is the di-atomic form ($O_2$). Ozone ($O_3$) and singlet oxygen ($^1O_2$) are forms of the gas that occur naturally and that can also be produced artificially. However, they are both unstable.

It is known to use ozone gas and singlet oxygen gas for the treatment of blood and human tissue. For example, ozone has been found effective against various viruses and fungi, and to inactivate a wide variety of bacteria including Pseudomonas Aeruginosa, Staphylococcus Aureus and Mycobacterium Tuberculosis. The administration of ozone is also thought to have beneficial effects on a person's health in general by way of stimulating oxygen metabolism. Studies of the effects of treatment using singlet oxygen indicate similar or even more dramatic effects. It has also been shown that the administration of ozone and singlet oxygen to a healthy person, through direct inhalation, can be beneficial.

One very important use of ozone and singlet oxygen is in the sterilization of blood, for example, blood for transfusion. Through the use of ozone and singlet oxygen, it is possible to deactivate a variety of potential vital contaminants of blood, including HIV-1 and Hepatitis.

It is known to introduce ozone and singlet oxygen directly to diseased tissue. Alternatively, the ozone and singlet oxygen may first be introduced to a carrier liquid such as USP water or blood, and then the carrier liquid may be introduced to the diseased tissue or into a person's bloodstream, as appropriate. Blood may be drawn from the person treated and then infused or injected back into the person.

Treatment of blood with ozone or singlet oxygen presents a number of problems. Prior art blood oxygenators may cause frothing of the blood or the formation of bubbles, which is undesirable, and also can lead to haemolysis—the destruction of the cell walls of the red blood cells and the subsequent loss of hemoglobin therefrom.

BRIEF DESCRIPTION OF THE INVENTION

An object of the present invention is to provide a gas/liquid contact apparatus and method that address the problems of prior art oxygenators. A further aim is to provide an apparatus and method that may be used for contacting other gases and liquids.

A gas/liquid contact apparatus in accordance with the invention includes a chamber and fluid delivery means within the chamber having a spray orifice. The fluid delivery means includes a low pressure gas supply conduit extending to the orifice and liquid supply means communicating with the gas supply conduit upstream of the orifice. The fluid delivery means is adapted to cause liquid to be induced into and contacted with a gas stream flowing in the conduit and to issue from the orifice as a dispersed low pressure spray of liquid droplets. The apparatus also includes a film forming surface located within the chamber in the path of the spray of liquid droplets. The surface has a significant extent laterally of the orifice providing a substantial surface area for forming a film. The surface is relatively flat or slightly concave and is spaced from the spray orifice a distance selected so that the droplets impinge on the surface at relatively low velocity and form a film, for further contact with the gas.

A corresponding method is also provided.

It will be appreciated that, in the method and apparatus of the invention, there are essentially two gas/liquid contact zones. First contact occurs as the liquid is induced into the gas stream in the fluid delivery means. The liquid droplets are then sprayed onto the film forming surface and form a film, providing further opportunity for contact with the gas. Accordingly, it is believed that, for example, in the field of blood treatment, the method and apparatus of the invention will provide for efficient oxygenation of the blood. The fact that the liquid issues from the spray orifice as a dispersed low-pressure spray of liquid droplets and that the droplets then impinge on the film forming surface at relatively low velocity, avoids the destructive effects that have occurred with prior art blood oxygenators. Provided the apparatus is operated correctly, bubbling and frothing of the blood is avoided.

The apparatus of the invention may be designed to operate on either a "one pass" or "recirculation" basis. In a one pass apparatus, blood is continuously delivered to and withdrawn from the apparatus and is treated only during the time that it passes through the apparatus. This type of arrangement may be suitable, for example, for treating blood as part of a sterilization program in a blood transfusion service. Blood may be transferred "bag-to-bag" with the apparatus located between the two bags for treating the blood as it flows from one to the other.

In a recirculation type of apparatus, the blood is essentially treated on a "batch" basis. In other words, a measured quantity of blood is introduced into the apparatus and treated for a selected period of time, following which the apparatus is emptied and the blood used.

BRIEF DESCRIPTION OF DRAWINGS

In order that the invention may be more clearly understood, reference will now be made to the accompanying drawings, which illustrate a number of preferred embodiments of the invention by way of example and with reference to the prior art. In the drawings:

FIGS. 2 and 4 show "one pass" type oxygenators, while FIG. 3 shows a recirculation type.

DESCRIPTION OF THE PRIOR ART

Figure 1:
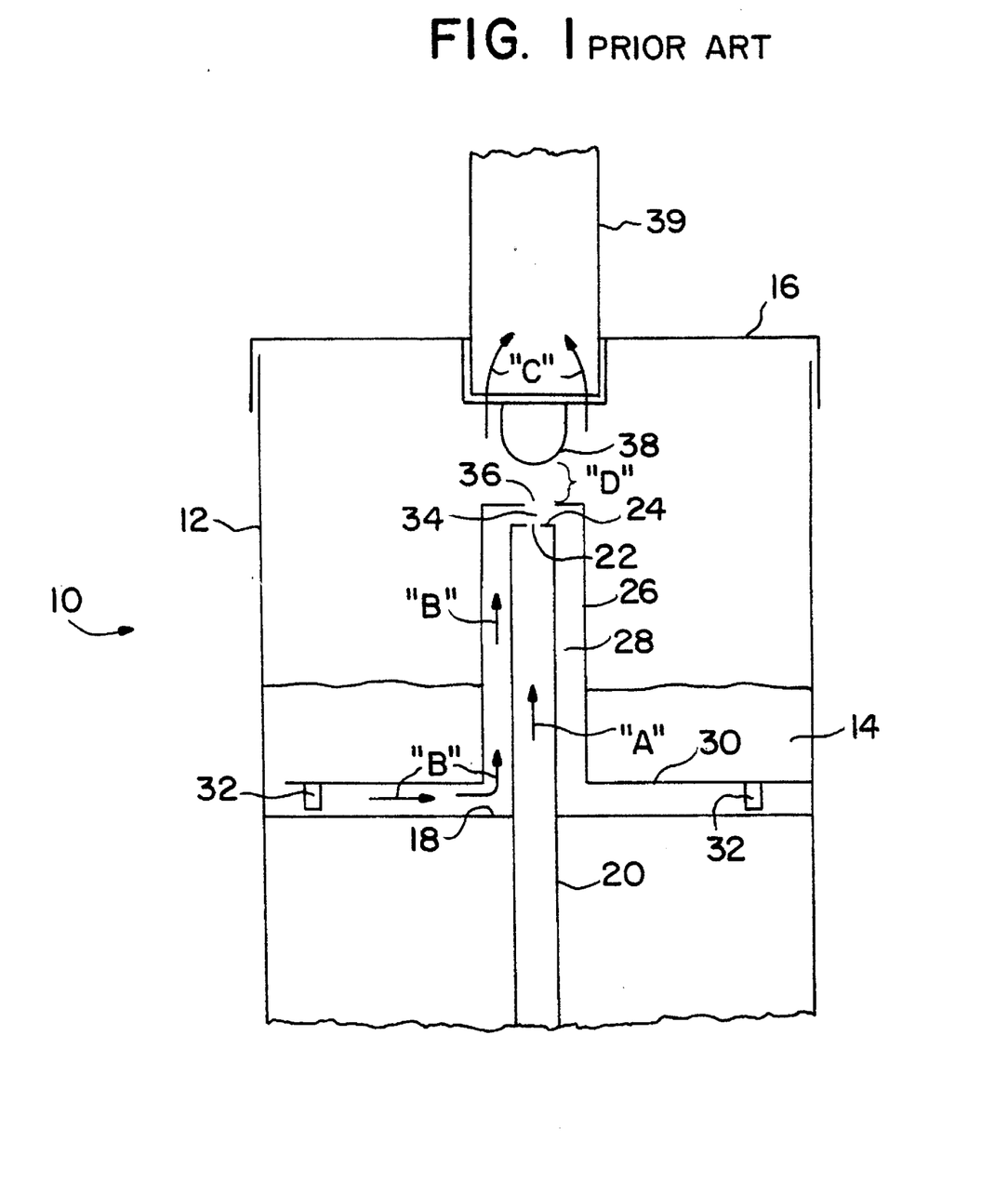
FIG. 1 is a diagrammatic vertical sectional view through a so-called "nebulizer" forming part of the prior art.

The nebulizer shown in FIG. 1 is typically used in an inhaler used to introduce certain types of medicine into the lungs of a patient by inhalation. The nebulizer 10 comprises a main chamber 12 that is adapted to hold a quantity of liquid medicine 14. The main chamber 12 is closed off by a cap member 16. At the opposite end thereof is a floor 18 with an oxygen inlet 20 extending therethrough, and that is adapted to allow for the flow of oxygen into the main chamber 12 as shown by arrow "A". The oxygen inlet 20 has a gas introduction orifice 22 in the end portion 24 thereof. A removable channelling member 26 is located within the main chamber 12, and defines an annular passageway 28 for the liquid medicine 14 to reach the gas introduction orifice 22 as shown by arrows "B". The horizontally oriented base portion 30 of the channelling member 26 has a plurality of small feet 32 depending therefrom, which feet 32 raise the level of the base portion 30 above the floor 18 of the main chamber 12, so as to allow the liquid medicine 14 to reach the annular passageway 28.

When the oxygen gas flows through the oxygen inlet 20 and then through the gas introduction orifice 22, a low pressure area is created in the area around the space 34 between the nebulizing orifice 36 and the gas introduction orifice, which causes the liquid medicine 14 to be drawn up the annular passageway 28, to the space 34. The oxygen flow impacts the liquid medicine that reaches this space 34 and sprays it through the nebulizing orifice 36 so as to impact on the impact member 38, and thereby nebulize the liquid medicine 14. The flow of nebulized oxygen gas continues through the outlet 39 as shown by arrows "C". Any of the liquid medicine 14 that is not carried by this flow of oxygen drops back down into the liquid medicine 14. This process continues until all of the liquid medicine 14 is nebulized into a fine mist and carried by the oxygen flow through the outlet 39.

Nebulizers such as that shown in FIG. 1 are unsuitable for treating blood because of the "destructive" effect on the blood that would result from the blood being directed against the impact member 38. The liquid carried by the flow of oxygen impacts quite strongly on the impact member 38, causing foaming and bubbling. Further, such high impact can readily cause damage to the cell walls of the red blood cells.

DESCRIPTION OF THE PREFERRED EMBODIMENTS

Figure 2:
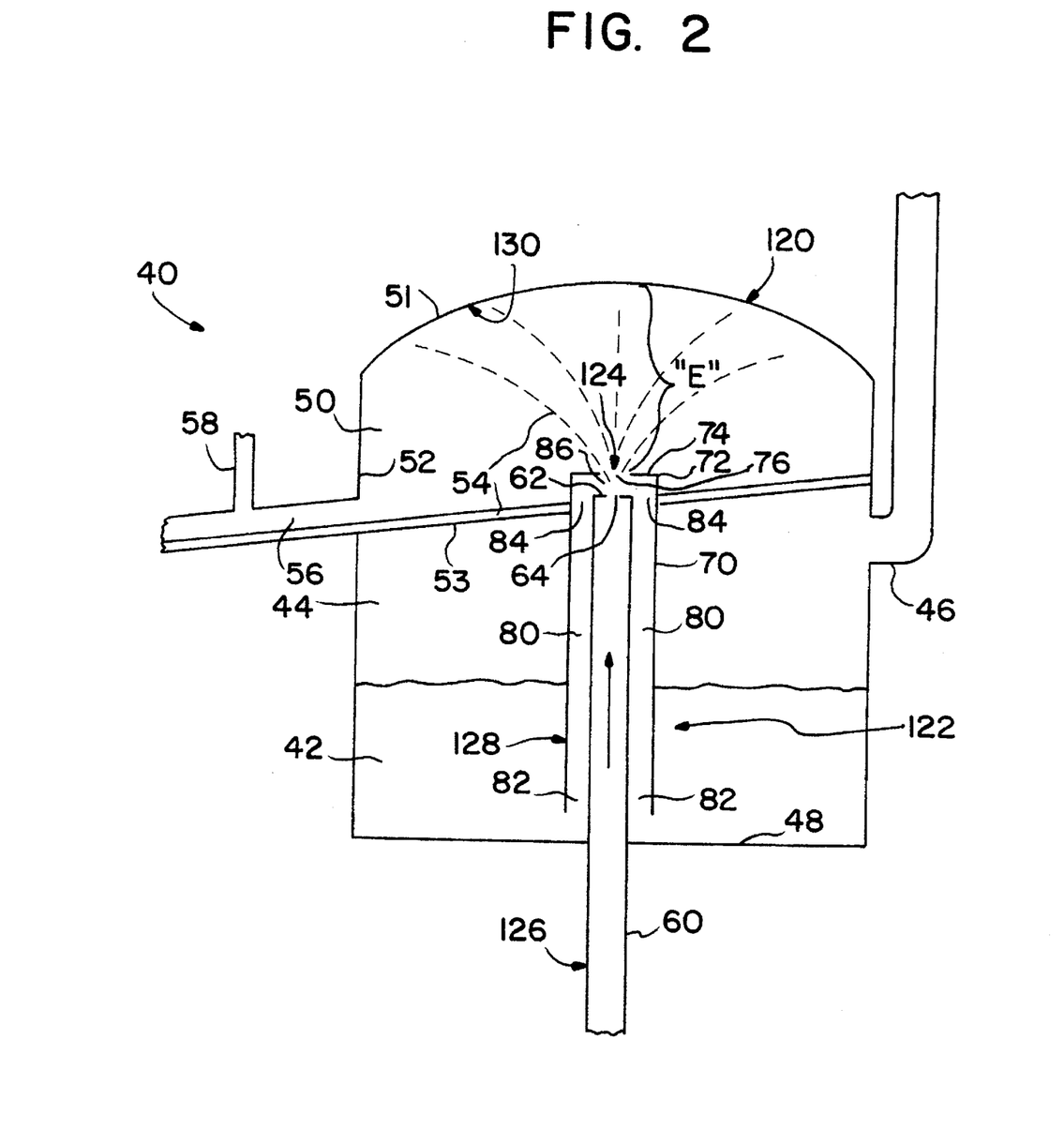
FIGS. 2, 3 and 4 are similar views through blood oxygenators in accordance with the invention.

Reference will now be made to FIG. 2, which shows one embodiment of an oxygenation apparatus of the present invention in use. The oxygenation apparatus is denoted 40 and is used to introduce oxygen gas into a carrier liquid 42 in a one-pass operation.

The oxygenation apparatus 40 comprises a receiving chamber 44 for receiving the carrier liquid 42 therein and a carrier liquid inlet 46 for introducing the carrier liquid 42 to be oxygenated into the receiving chamber 44. The carrier liquid 42 can be introduced through the carrier liquid inlet 46 on a continuous basis or in discrete amounts. The carrier liquid 42 collects in the bottom 48 of the receiving chamber 44.

Above the receiving chamber 44 is a contacting chamber 50 that allows for oxygen gas molecules to thoroughly contact the carrier liquid 42, in a manner that will be described in greater detail subsequently. The contacting chamber 50 has a generally concave top portion 51 that is thereby adapted to receive a spray of carrier liquid 42, as will be described subsequently.

There is a separating partition 53 located between the receiving chamber 44 and the contacting chamber 50. The separating partition 53 is adapted to substantially physically separate the receiving chamber 44 and the contacting chamber from each other. In this manner, oxygenated carrier liquid 54 in the contacting chamber 50 is a precluded from returning to the receiving chamber 44, thereby allowing the oxygenation apparatus 40 of the present invention to provide a one-pass type operation. The separating partition 53 preferably slopes downwardly to allow the oxygenated carrier liquid 54 to flow therealong to an oxygenated carrier liquid outlet 56 that allows the oxygenated carrier liquid 54 to exit from the contacting chamber 50. The oxygenated carrier liquid outlet 56 is attached to a standard receptacle (not shown) of a type that is suitable for collecting the oxygenated carrier liquid 54. Extending upwardly from a top portion of the oxygenated carrier liquid outlet 56 is a one-way oxygen gas vent 58 for allowing any of the oxygen gas molecules that have passed into the contacting chamber 50 to vent to the ambient surroundings.

At the bottom 48 of the receiving chamber 44 is an oxygen gas inlet 60 for introducing oxygen gas molecules into the oxygenation apparatus 40. The oxygen gas molecules are introduced at a gas pressure slightly above the ambient surrounding air pressure—typically in the order of a few inches of $H_2O$ gauge pressure—so as to cause a flow of the oxygen gas molecules from the oxygen gas inlet 60 into the contacting chamber 50 and then out of the contacting chamber 50 through the oxygenated carrier liquid outlet 56. The gas pressure within the contacting chamber 50 is at a level between the gas pressure within the oxygen gas inlet 60 and the gas pressure of the ambient surroundings. The end portion 62 of the oxygen gas inlet 60 has a gas introduction orifice 64 therein, which is fairly small in diameter—perhaps about 0.5 mm—and is thereby adapted to cause a jet of oxygen gas molecules to be emitted therefrom.

An annular wall member 70 extends downwardly from the separating partition 53 to within a small distance—perhaps about 1.0 mm or even less—from the bottom 48 of the receiving chamber 44. Preferably, the separating partition 53 is extended upwardly at the annular wall member 70 so as to allow the top end 72 of the annular wall member 70 to be generally above the level of the rest of the separating partition 53. The top end 72 of the annular wall member 70 terminates in a flow restricting portion 74 that has a spray orifice 76 centrally located therein. The spray orifice 76 is preferably about 1.0 mm in diameter. In any event, the spray orifice 76 should be larger in diameter than the gas introduction orifice 64 so as to allow all of the gas emitted from the gas introduction orifice 64 to pass through the spray orifice 76 without impinging on the flow restricting portion 74.

The annular wall member 70 encircles and substantially covers the oxygen gas inlet 60 and defines a passageway 80 around the oxygen gas inlet 60. The passageway 80 is oriented so as to extend substantially vertically upwardly and has a first end 82 located at the bottom thereof and a second end 84 located at the top thereof. The passageway 80 connects at the first end 82 thereof to the receiving chamber 44 in fluid communication with the space 86 that is located between the gas introduction orifice 64 and the spray orifice 76 at the second end 84 thereof.

In use, oxygen gas molecules are fed into the oxygen gas inlet 60 at a pressure that is slightly above ambient pressure. It is important to use a gas pressure that is only slightly above ambient air pressure, which therefore keeps the rate of flow of oxygen gas molecules quite low, so as to preclude any foaming or bubbling of the carrier liquid 42, or in the event that the carrier liquid 42 is blood, to preclude any damage to the haemoglobin cell walls. The flow of oxygen gas molecules exits the oxygen gas inlet 60 through the gas introduction orifice 64 as a jet of oxygen gas molecules. This jet of oxygen gas molecules causes a low gas pressure area between the gas introduction orifice 64 and the spray orifice 76, which in turn draws the carrier liquid 42 in the receiving chamber 44 up the passageway 80 until it reaches the space 86. Once the carrier liquid 42 reaches this space 86, it is impacted by the jet of oxygen gas molecules exiting the gas oxygen inlet through the gas introduction orifice 64. The carrier liquid 42 is thereby sprayed through the spray orifice 76 into the separating partition 53. Resultingly, the oxygen gas molecules thoroughly contact the carrier liquid 42 so as to thereby oxygenate the carrier liquid 42.

The spray of oxygen gas molecules and carrier liquid 42 typically impacts on the generally concave top portion 51 of the contacting chamber 50, so as to cause increased contact of the oxygen gas molecules and the carrier liquid 42. The top portion 51 is preferably at a distance "E" from the spray orifice 76 that is sufficient to cause the spray of carrier liquid 42 from the spray orifice 76 to slow down considerably so as to significantly reduce the impact of the carrier liquid 42 on the top portion 51. The carrier liquid 42 then either drips off the top portion 51 of the contacting chamber 50 or flows down the inner walls 52 of the contacting chamber 50, and collects on the separating partition 53. The spray orifice 76 is located substantially above the level of the rest of the separating partition 53 so as to maintain any volume of oxygenated carrier liquid 54 on the separating partition 53 below the level of said spray orifice 76, and thereby preclude any oxygenated carrier liquid 54 from entering the spray orifice 76 and subsequently mixing with the untreated carrier liquid 42 therebelow.

In other words, the apparatus shown in FIG. 2 is a gas/liquid contact apparatus that includes means 120 defining a chamber, fluid delivery means 122 within the chamber having a spray orifice 124 and including a low pressure gas supply conduit 126 extending to the orifice, and liquid supply means 128 communicating with the gas supply conduit 126 upstream of the orifice. The fluid delivery means is adapted to cause liquid to be induced into and contacted with a gas stream flowing in the conduit 126 and to issue from the orifice 124 as a dispersed low-pressure spray of liquid droplets.

The apparatus also includes a film forming surface 130 located within the chamber in the path of the spray of liquid droplets. The surface has a significant extent laterally of the orifice and is relatively flat or slightly concave and spaced from the spray orifice a distance selected so that the droplets impinge on the surface at relatively low velocity and form a film on the surface for further contact with the gas.

Figure 3:
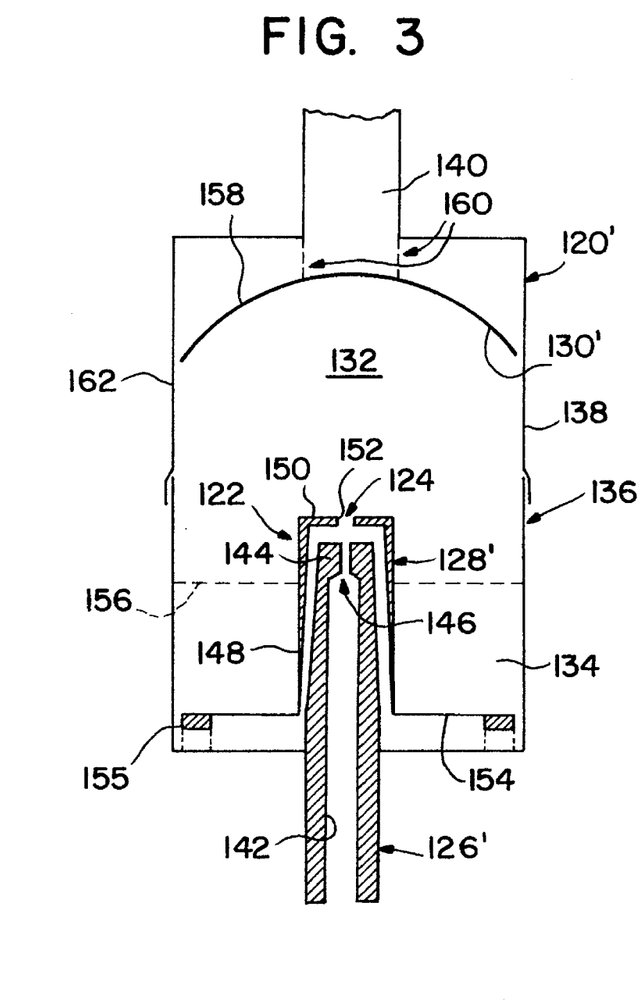
Figure 4:
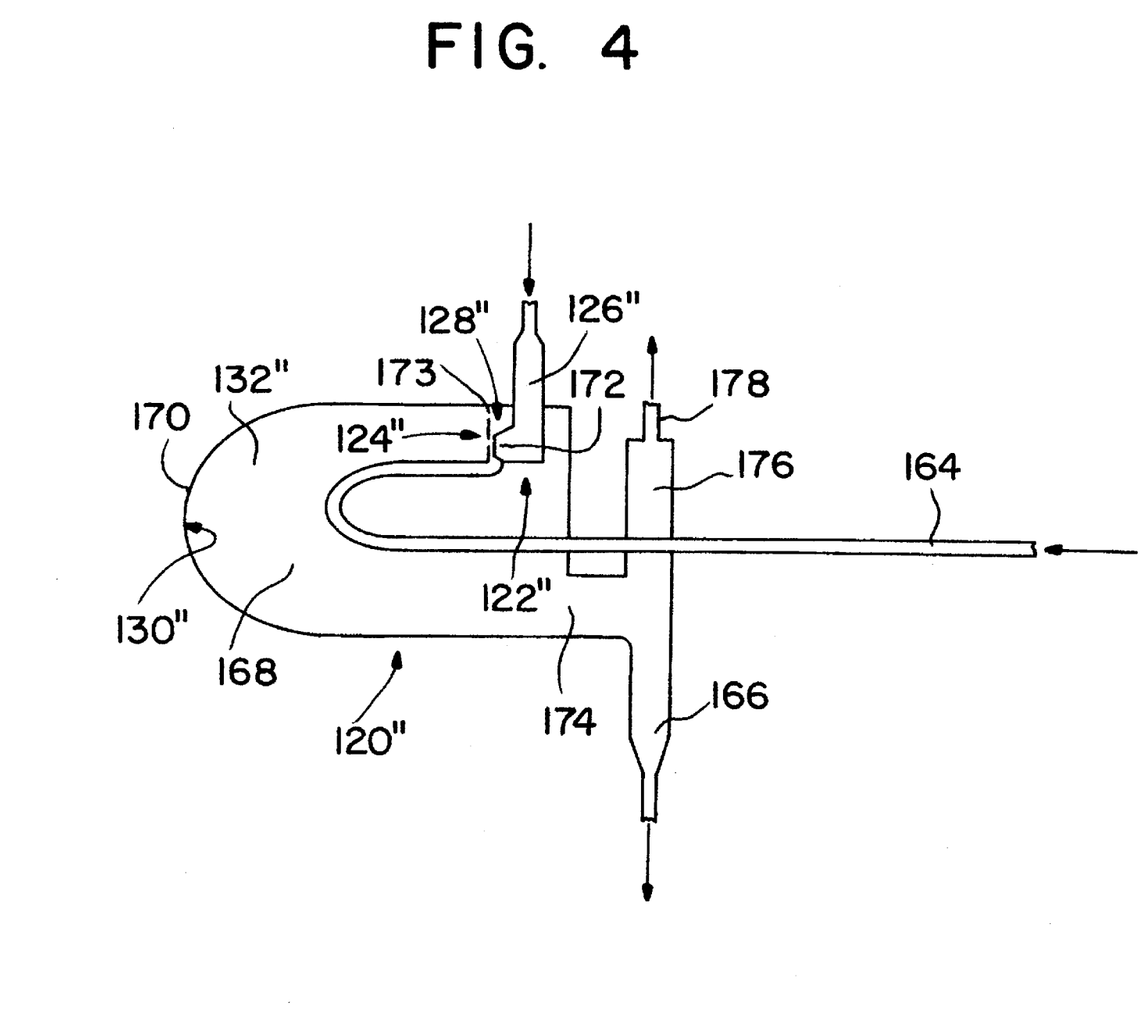

FIG. 3 shows a gas/liquid contact apparatus in the form of a blood oxygenator, of the recirculating type. In other words, a quantity of blood is introduced into the apparatus, treated and then removed. FIG. 4 on the other hand shows another embodiment of a "one-pass" type of apparatus that may be used for "bag-to-bag" treatment of blood. The apparatus shown in each of FIGS. 3 and 4 includes the same principal elements as the elements identified by reference numerals 120 to 130 in FIG. 2. Those same elements but with prime and double prime superscripts respectively will be used in FIGS. 3 and 4 to denote the same elements.

Referring first to FIG. 3, the apparatus includes a housing 120' defining a chamber 132 for containing blood 134 to be oxygenated. The housing is essentially cylindrical in shape and comprises a lower portion 136 made of a relatively rigid plastic material and a complimentary cap portion 138 that is made of a somewhat more resilient plastic material and that is capable of being snap-fitted over the lower housing portion 136 to provide a liquid-tight seal between the two portions. The cap is also generally cylindrical and has a cylindrical sleeve 140 at the top which serves as an outlet to an ozone destruct unit in which excess ozone is disposed of. A measured volume of blood to be treated is introduced into the lower housing portion 136, for example, by pipette after removing the cap 138. While the apparatus may be made in different sizes depending on the amount of blood to be treated, the particular example shown is designed for treating small amounts of blood, for example, as low as 5 or 10 ml. Treatment time may vary, e.g. from 45 seconds to 60 minutes.

As noted previously, the apparatus includes fluid delivery means 122' including a low pressure gas supply conduit 126'. In this embodiment, conduit 126' is a simple plastic tube that is fitted into the bottom wall of the lower housing portion 136 so as to extend vertically upwardly inside the housing generally on its longitudinal axis. The tube has an internal passageway 142 provided with a restriction 144 at its upper end so that the gas leaves the conduit through a restricted opening 146.

Liquid supply means 128' of the apparatus is provided by a sleeve 148 that concentrically surrounds the portion of the gas supply conduit 126' within chamber 132. A transverse wall 150 at the top of sleeve 148 is provided with an opening 152 that is aligned with the restricted opening 146 of gas supply conduit 126' and that provides the spray orifice 124' of the apparatus.

Sleeve 148 is supported at its lower end by an outwardly directed flange 154 that is supported generally parallel to and at a spacing above the bottom wall of housing 136 by a series of "feet" 155 that are spaced around the perimeter of the flange so as to allow unrestricted entry of blood to the interior of sleeve 148. Thus, when there is no gas flow through conduit 126' but there is blood 134 in housing 136, the blood will adopt a natural level that is the same both inside and outside of sleeve 148. The dotted line denoted 156 indicates a maximum recommended blood level within the housing. The blood level should never be above the upper end of sleeve 148, otherwise excessive bubbling and foaming will occur in use.

When oxygen is introduced through conduit 126', the restriction 144 at the upper end of the conduit acts like a venturi, causing the velocity of the gas leaving the conduit to increase, and forming a low pressure zone between the conduit opening and the spray orifice 124'. This will cause liquid to be induced into the gas stream, providing for a first area of contact between the oxygen and the blood.

In this embodiment, the film forming surface 130' of the apparatus is provided by the underside of a dome-shaped member 158 that is supported within the cap 138 by plastic webs indicated at 160. Thus, the surface is located within the chamber in the path of the spray of liquid droplets from spray nozzle 124' and has a significant extent laterally of the orifice. In this embodiment, the dome-shaped member is circular in plan to match the cylindrical configuration of the housing 136. The diameter of the dome-shaped member is slightly less than the internal diameter of the housing to allow an annular gap 162 through which excess oxygen (probably including ozone) can escape to outlet 140.

The film forming surface 130' is spaced from the spray orifice 124' a distance selected so that the droplets impinge on the surface at relatively low velocity and form a film on the surface for further contact with the gas. The dome shape of the surface tends to cause the droplets that form on the surface to migrate outwardly towards the perimeter of the dome-shaped member, where they can fall back into the lower portion of the housing. It is desirable to avoid droplets falling onto the spray orifice 124' because of the possible destructive effect on the blood cells that could result from direct impingement thereon of the gas stream from conduit 126'.

For the same reason, it is important that the pressure of the oxygen supply should be kept relatively low; otherwise the blood cells could be damaged either at the point of induction of the blood into the gas stream, or due to the blood being driven with excessive force against the film forming surface 130'. In practice, a gas delivery pressure in the range 0.5 to 4 psi is believed to be appropriate. In comparison, a prior art nebulizer of the form shown in FIG. 1 might require a pressure of 10 to 15 psi for effective operation.

The blood flow rate in the apparatus of the invention may be in the range 0.25 L/min to 5.0 L/min. Again, this compares with a flow rate of 5 L/min to 12 L/min for a prior art nebulizer.

The spacing between the spray orifice 124' and the highest point of the dome-shaped member 158 may be of the order of 12.5 mm, compared with a distance of about 0.2 mm between the impact member 38 and the nebulizing orifice 36 of the nebulizer shown in FIG. 1.

The diameter of the spray orifice 124' should be approximately 1.6 times the diameter of the diameter of the restricted opening 146 in the gas supply conduit. For example, in a practical embodiment, the spray orifice may have a diameter of 0.91 mm and the opening 136 a diameter of 0.57 mm.

These dimensions would relate to a chamber 132 having an overall height to the centre of the dome-shaped member 158 of approximately 35 mm, and an internal diameter also of 35 mm.

Similar dimensions and operating parameters also apply to the other embodiments of the invention.

The oxygen supply to the apparatus will be medical grade and preferably will include both diatomic and triatomic oxygen ($O_2$ and $O_3$). The relative concentrations of the two forms of oxygen will be adjusted as appropriate.

Referring now to FIG. 4, a "bag-to-bag" one-pass form of the apparatus is shown. Blood to be treated is delivered through a tube 164 from a first blood bag (not shown) and treated blood is withdrawn through an outlet 166 and delivered to a receiving blood bag (also not shown). In this case, the housing 120" defining the chamber 132" has a horizontal configuration, as compared with the vertical configuration of FIG. 3. The housing is made of an appropriate plastic material has a dome-shaped wall 170 at one side that provides a concave film forming surface 130". In this case, the fluid delivery means 122" has a spray orifice 124" that is laterally directed towards surface 130". It will be seen that the orifice is not in fact located on the centre line of chamber 168 but is positioned to direct a spray against an upper portion of the concave film forming surface so that the droplets will form a film and gradually migrate down the surface by gravity; like the embodiment of FIG. 3, the droplets will not drip back onto the spray orifice.

In the embodiment of FIG. 4, the gas supply conduit 126" enters chamber 168 from above and has a laterally directed opening 172 that is also restricted and aligned with spray orifice 124" (again like the embodiment of FIG. 3). The liquid supply means 128" is in this case defined by a housing 173 that forms an enclosure around the gas supply conduit opening 172, and in which the spray orifice 124" is formed. The housing communicates with the blood inlet pipe 164. Blood outlet pipe 166 communicates with an opening 174 at the bottom of the end wall of housing 168 remote from the film forming surface 130". Thus, the oxygenated blood that forms a film on surface 130" and migrates down that surface naturally flows into the blood outlet tube 166. A vent pipe 176 extends upwardly from tube 166 and has an outlet 178 through which excess gas is delivered to an ozone destruct unit.

The apparatus shown in FIG. 4 operates in essentially similar fashion to the previous embodiments. An $O_2/O_3$ gas mixture is introduced through conduit 126" at relatively low pressure and induces blood from tube 164, which is then sprayed as droplets through orifice 124". A first gas/blood contact zone is established at the point of liquid induction. The liquid droplets from spray orifice 124" impinge at relatively low velocity on surface 130" and form a film on that surface, permitting further contact with gas within chamber 168. Again, the gas pressure may in the range 0.5 to 4 psi.

It will of course be appreciated that the preceding description relates to particular preferred embodiments of the invention and that modifications are possible within the broad scope of the invention. For example, the particular parameters and dimensions given are by way of example only and are not intended to be limiting. As noted previously, while reference has been made primarily to the oxygenation of blood, the invention may be applied to the contacting of other gases and liquids.

Specific structural changes may of course be made. For example, liquid could be conducted directly into the restricted opening at the inner end of the gas supply conduit (e.g. the opening 146 in FIG. 3) in which case the outer end of that opening will also serve as the spray orifice of the fluid delivery means.

In the specific embodiments disclosed, the film forming surface is slightly concave. In embodiments in which the surface is disposed above the spray orifice this is necessary in order to minimize the risk of droplets of liquid falling back onto the spray orifice. In an embodiment such as FIG. 4 in which the spray of liquid droplets is directly laterally onto the surface, the surface could be flat. In either event, the surface should have a significant extent laterally of the orifice so as to allow formation of a film on the surface.

I claim:

1. Gas/liquid contact apparatus comprising:
   means defining a chamber for receiving and collecting the liquid being contacted with said gas;
   fluid delivery means within said chamber having a spray orifice and including a gas supply conduit having a discharge providing a gas flow through said orifice, and liquid supply means connected to the liquid to be gas contacted and communicating with said gas flow between the conduit discharge and orifice, the reduced pressure created by the gas flow between said discharge and orifice causing said liquid to be induced into and contacted with a gas stream flowing in said conduit and to issue from said orifice as a dispersed spray of liquid droplets; and
   a spray collection surface located within said chamber in the path of said spray of liquid droplets, said surface being spaced from said spray orifice a distance selected so that said droplet impinge thereon at relatively low velocity and form a film for further contact with the gas; said surface being shaped and positioned with respect to said orifice and chamber, and having sufficient dimensions transverse to the nozzle axis to intercept, capture and return to said chamber as gasified liquid substantially the entirety of the droplets of gasified liquid, and said droplets thereby being precluded from exiting said chamber by axial directed movement away from said nozzle.

2. Apparatus in accordance with claim 1, wherein said spray collection surface has a significant extent laterally of said orifice and is relatively flat or somewhat concave.

3. Apparatus in accordance with claim 1 which is designed to operate on a one-pass basis, wherein said means defining a chamber comprises a housing having liquid outlet means, wherein said liquid supply means is arranged to continuously supply liquid for contact with said gas, and wherein the apparatus is adapted to permit liquid which has been so contacted, to flow to said liquid outlet means.

4. Apparatus in accordance with claim 3, wherein said means defining a chamber comprises a housing having a lateral end wall with an inner surface defining said film forming surface, wherein said fluid delivery means is arranged to direct said spray of liquid droplets laterally towards said surface so that the droplets form said film on the surface and migrate down the surface when the apparatus is in use, said liquid outlet means comprising an outlet from said housing located to receive said liquid migrating down said film forming surface, and wherein said liquid inlet means comprises a liquid supply tube having an outer end externally of said housing, and an inner end communicating with a said spray orifice, wherein said gas supply conduit has an outer end externally of said housing, and an inner end within the housing having a restricted opening disposed at a spacing from and aligned with said spray orifice, said spray orifice being defined by an opening in a housing surrounding said inner end of the gas supply conduit and communicating with said liquid inlet tube.

5. An apparatus as claimed in claim 3, wherein said housing has a lower portion for containing a body of said liquid, and an upper portion which includes said film forming surface, said fluid delivery means being disposed within said chamber so that said spray orifice is above a maximum liquid level within said housing for directing said spray of liquid droplets towards said film forming surface, and wherein said liquid supply means includes a liquid inlet to said housing through which liquid can be added to said body, and means defining a liquid passageway from said body of liquid and providing said communication with the gas supply conduit upstream of the spray orifice so that, in use, liquid is induced through said passageway from said body of liquid by a gas stream flowing in said conduit, and wherein the apparatus further includes a partition extending across said housing below the level of said spray orifice and above the said maximum liquid level and arranged so that liquid sprayed through said nozzle is prevented from returning to said body of liquid, said liquid inlet to the housing being disposed below said partition, and said liquid outlet means being disposed above said partition and arranged so that liquid that collects on said partition flows to said liquid outlet means.

6. Apparatus in accordance with claim 5, wherein said gas supply conduit extends in a generally upright position in said housing from an outer end externally of the housing to an inner end which is within the housing and has a restricted opening disposed immediately below said spray orifice, said means defining a liquid passageway comprising a sleeve extending around said gas conduit, whereby the liquid passageway has an annular configuration, said sleeve having an open lower end communicating with said body of liquid and through which liquid can enter said passageway, and an upper end having an end wall extending across and spaced above said inner end of the conduit, said wall being provided with an opening defining said spray orifice, whereby a gas stream flowing in said conduit is accelerated in said restricted opening, inducing liquid to flow through said passageway for contact with said gas and formation of said liquid droplets of said low pressure spray.

7. Apparatus in accordance with claim 6, wherein said spray orifice has a diameter approximately 1.6 times the diameter of the restricted opening of the gas supply conduit.

8. Apparatus in accordance with claim 5, which is designed to operate on a liquid recirculation basis, wherein said means defining a chamber comprises a housing having a lower portion for containing a body of liquid and an upper portion which includes said film forming surface, wherein said fluid delivery means is disposed within said chamber with said spray orifice above a maximum level of said body of liquid and arranged to direct said spray of liquid droplets upwardly against said film forming surface, said surface being concave and of such lateral extent that liquid droplets adhering to said surface tend to migrate outwardly and fall from said surface away from said spray orifice, said housing being adapted to permit introduction of said body of liquid to the housing and withdrawal of said body of liquid from the housing after contacting with said gas, the housing further including gas vent means.

9. Apparatus in accordance with claim 8, wherein said film forming surface is defined by the inner surface of a dome-shaped member which is disposed in said upper portion of the housing, and wherein said gas vent comprises an outlet in said upper portion of the housing communicating with said chamber around the perimeter of the dome-shaped member.

10. Apparatus in accordance with claim 8, wherein said upper portion of the housing is removable from the lower portion of the housing for introduction and removal of said body of liquid, and wherein said housing upper and lower portions are adapted to engage in liquid-tight fashion to define said chamber.

11. Apparatus in accordance with claim 8, wherein said gas supply conduit extends in a generally upright position in said housing from an outer end externally of the housing to an inner end which is within the housing and has a restricted opening disposed immediately below said spray orifice, said means defining a liquid passageway comprising a sleeve extending around said gas conduit, whereby the liquid passageway has an annular configuration, said sleeve having an open lower end communicating with said body of liquid and through which liquid can enter said passageway, and an upper end having an end wall extending across and spaced above said inner end of the conduit, said wall being provided with an opening defining said spray orifice, whereby a gas stream flowing in said conduit is accelerated by said restricted opening, including liquid to flow through said passageway for contact with said gas and formation of said liquid droplets which issue through said spray orifice as said low pressure spray.

12. Apparatus in accordance with claim 11, wherein said spray orifice has a diameter approximately 1.6 times the diameter of the restricted opening of the gas supply conduit.

13. A method of contacting a gas and a liquid, comprising:

introducing a low pressure stream of said gas into a chamber through a spray orifice, while inducing said liquid into the gas stream in a first liquid/gas contact zone; and causing said liquid to issue from said spray orifice as a dispersed low-pressure spray of liquid droplets; and in intercepting, capturing and returning to said chamber substantially the entirety of the droplets having been contacted with said gas in said first zone, by directing said spray against a film forming surface located within said chamber in the path of said spray of liquid droplets and at a distance selected so that said droplets impinge on said surface at relatively low velocity and form a film on said surface for providing a further gas/liquid contact zone, and said surface being shaped and positioned with respect said spray orifice and chamber, and having sufficient dimensions transverse to the spray orifice axis, to enable said interception, capture and return to said chamber of said substantially entirety of droplets, and said droplets thereby being precluded from exiting said chamber by axial directed movement away from said orifice.

14. A method of contacting blood with an oxygenating gas comprising:

introducing a low pressure stream of oxygen comprising $O_2$ and $O_3$ into a chamber through a spray orifice, while inducing blood into the oxygen stream in a first blood/oxygen contact zone; and causing said blood to issue from said spray orifice as a dispersed low pressure spray of blood droplets; and intercepting capturing and returning to said chamber substantially the entirety of the droplets having been contacted with said gas in said first zone, by directing said spray against a film forming surface located within said chamber in the path of said spray of blood droplets and at a distance selected so that said droplets impinge on said surface at relatively low velocity and form a film on said surface for providing a further oxygen/blood contact zone and said surface being shaped and positioned with respect to said spray orifice and chamber, and having sufficient dimensions transverse to the spray orifice axis, to enable said interception capture and return to said chamber of said substantially entirety of droplets, and said droplets thereby being precluded from exiting said chamber by axial directed movement away from said orifice.

15. A method in accordance with claim 14, wherein oxygen is introduced at a pressure in the range 0.5 to 4 psi.

16. A method in accordance with claim 15, wherein blood is induced into the oxygen stream at a flow rate in the rate 0.25 L/min to 5.0 L/min.

17. Apparatus for effectively oxygenating blood while avoiding hemolysis, comprising:

a chamber for receiving and collecting blood being oxygenated:

blood delivery means within said chamber having a spray orifice and a gas supply conduit having a discharge providing a gas flow through said orifice, and blood supply means communicating with the gas flow between the conduit discharge and orifice, the reduced pressure created by gas flow between said discharge and orifice causing blood to be induced into and contacted with an oxygenating gas stream flowing from said conduit to said orifice, and to issue from the orifice as a dispersed low-pressure spray of blood droplets; and a spray collection surface being located within said chamber in the path of said spray of blood droplets, said surface being spaced from said spray orifice a distance selected so that said droplets impinge thereon at relatively low velocity and form a film for further contact with the oxygenating gas while minimizing impact damage to the blood; said surface being shaped and positioned with respect to said orifice and chamber, and having sufficient dimensions transverse to the orifice axis, to intercept, capture and return to said chamber as oxygented blood substantially the entirety of the droplets of oxygenated blood, and said droplets thereby being precluded from exiting said chamber by axial directed movement away from said orifice.

18. Apparatus in accordance with claim 17, wherein the pressure of the oxygenating gas in said conduit is from 0.5 to 4 psi.

19. Apparatus in accordance with claim 17 further including blood outlet means at said chamber, disposed to receive the blood collected at said surface and enables its withdrawal from the apparatus.

20. Apparatus in accordance with claim 19, wherein said outlet means is disposed to receive the collected blood by gravitational flow.

21. A method for effectively oxygenating blood while avoiding hemolysis, comprising:

providing a chamber having a spray orifice and a gas supply conduit the discharge from which provides a gas flow through said orifice;

establishing an oxygenating gas stream flow from said conduit to said orifice;

feeding a blood supply to the gas flow between the conduit discharge and orifice, the reduced pressure created by said gas flow between said discharge and orifice causing blood to be induced into and contacted with the said oxygenating gas stream and to issue from the orifice as a dispersed low pressure spray of blood droplets; and intercepting and collecting substantially the entirety of the droplets of oxygenated blood, by means of a spray collection surface located within the chamber in the path of said spray of blood droplets, said surface being spaced from said spray orifice a distance selected so that said droplets impinge thereon at relatively low velocity and form a film for further contact with the oxygenating gas while minimizing impact damage to the blood; said surface being shaped and positioned with respect to said orifice and chamber, and having sufficient dimensions transverse to the orifice axis, to intercept, capture and return to said chamber as oxygented blood substantially the entirety of the droplets of oxygenated blood, and said droplets thereby being precluded from exiting said chamber by axial directed movement away from said orifice.

22. Apparatus in accordance with claim 21, wherein the oxygenating gas delivered in said conduit is at a pressure of from 0.5 to 4 psi.

23. A method in accordance with claim 21, further including accumulating the blood collected at said surface and withdrawing it from the apparatus.

24. A method in accordance with claim 23, wherein the collected blood from said surface is accumulated by gravitational flow.

* * * * *